: US 12,409,222 B2
(45) Date of Patent: Sep. 9, 2025

(12) United States Patent
Cao

(54) METHOD FOR PREPARING GALACTO-OLIGOSACHARIDES FROM LACTULOSE

(71) Applicant: FrieslandCampina Nederland B.V., Amersfoort (NL)

(72) Inventor: Linqiu Cao, Wageningen (NL)

(73) Assignee: FrieslandCampina Nederland B.V., Amersfoort (NL)

( * ) Notice: Subject to any disclaimer, the term of this patent is extended or adjusted under 35 U.S.C. 154(b) by 753 days.

(21) Appl. No.: 17/781,490

(22) PCT Filed: Dec. 2, 2020

(86) PCT No.: PCT/EP2020/084190
§ 371 (c)(1),
(2) Date: Jun. 1, 2022

(87) PCT Pub. No.: WO2021/110709
PCT Pub. Date: Jun. 10, 2021

(65) Prior Publication Data
US 2023/0026328 A1  Jan. 26, 2023

(30) Foreign Application Priority Data
Dec. 3, 2019 (EP) .................................. 19213166

(51) Int. Cl.
| | | |
|---|---|---|
| A61K 39/35 | (2006.01) | |
| A23L 33/00 | (2016.01) | |
| A23L 33/21 | (2016.01) | |
| A61K 31/202 | (2006.01) | |
| A61K 35/741 | (2015.01) | |
| C07H 3/06 | (2006.01) | |
| C12N 9/38 | (2006.01) | |
| C12P 19/12 | (2006.01) | |

(52) U.S. Cl.
CPC .............. *A61K 39/35* (2013.01); *A23L 33/21* (2016.08); *A23L 33/40* (2016.08); *A61K 31/202* (2013.01); *A61K 35/741* (2013.01); *C07H 3/06* (2013.01); *C12N 9/2471* (2013.01); *C12P 19/12* (2013.01); *C12Y 302/01023* (2013.01); *A23V 2002/00* (2013.01)

(58) Field of Classification Search
CPC ..................... C12N 9/2471; C12Y 302/01023
See application file for complete search history.

(56) References Cited

U.S. PATENT DOCUMENTS

2019/0119662 A1  4/2019  Hoshi

FOREIGN PATENT DOCUMENTS

| EP | 3399032 | 11/2018 |
|---|---|---|
| WO | 2019002304 | 1/2019 |

OTHER PUBLICATIONS

Rodriguez-Fernandez, Maria, et al.; "Detailed kinetic model describing new oligosaccharides synthesis using different B-galactosidases" Journal of Biotechnology, vol. 153, 2011, pp. 116-124.
Benitez-Paez, Alfonso, et al.; "Genome Structure of the Symbiont Bifidobacterium pseudocatenulatum CECT 7765 and Gene Expression Profiling in Response to Lactulose-Derived Oligosaccharides", Frontiers in Microbiology, Apr. 29, 2016, vol. 7, Article 624, pp. 1-16.
Kaneko, Kimiyuki, et al: "Development of hypoallergenic galacto-oligosaccharides on the basis of allergen analysis", Bioscience, Biotechnology, and Biochemistry, vol. 78, No. 1, Jan. 2, 2014, pp. 100-108.
Guerrero, Cecilia, et al.; "Optimisation of synthesis of oligosaccharides derived from lactulose (fructosyl-galacto-oligosaccharides) with [beta]-galactosidases of different origin"; Food Chemistry, Elsevier Ltd., NL, vol. 138, No. 4; Nov. 10, 2012; pp. 2225-2232.
International Search Report and Written Opinion, date of mailing Feb. 16, 2021; International Application No. PCT/EP2020/084190 (10 pgs.).

*Primary Examiner* — Thane Underdahl
(74) *Attorney, Agent, or Firm* — Fitch, Even, Tabin & Flannery LLP

(57) ABSTRACT

Process for the preparation of a galacto-oligosaccharide preparation, which process comprises the step of contacting a lactulose-containing feed with a beta-galactosidase derived from *Papiliotrema terrestris*. The resulting galacto-oligosaccharide is acceptable to subjects suffering from GOS-related allergy and subjects having lactose intolerance.

14 Claims, No Drawings
Specification includes a Sequence Listing.

SEQUENCE LISTING

<160> NUMBER OF SEQ ID NOS: 4

<210> SEQ ID NO 1
<211> LENGTH: 696
<212> TYPE: PRT
<213> ORGANISM: Cryptococcus terrestris

<400> SEQUENCE: 1

```
Met Ile Pro Ala Ser Ala Leu Leu Ala Ala Val Pro Leu Leu Ala Gln
1               5                   10                  15

Gln Val Ser Ala Gly Ile Leu Arg Arg Gln Asn Ala Ala Gly Ser Asp
            20                  25                  30

Ser Ala Ala Pro Asp Ser Ile Ala Asp Ala Ser Thr Gly Val Val Ser
        35                  40                  45

Ser Ile Ala Thr Glu Ala Val Ser Ser Gly Ala Thr Gly Leu Val Ala
    50                  55                  60

Ser Val Ala Met Ser Phe Ala Ser Ser Met Ala Thr Pro Thr Ala Thr
65                  70                  75                  80

Val Thr Gly Leu Ser Ser Glu Thr Gly Ala Pro Ser Asn Thr Pro Met
                85                  90                  95

Ala Ser Ala Ser Gly Ser Val Pro Thr Thr Thr Ser Ala Val Gly Ser
            100                 105                 110

Gly Asp Phe Asp Trp Val Gln Thr Asp Gly Leu Pro Thr Ile Thr Thr
        115                 120                 125

Thr Leu Ala Thr Thr Asn Gln Asp Ala Ile Thr Pro Thr Ala Thr Gly
    130                 135                 140

Pro Val Gly Gly Gln Gly Thr Pro Ala Val Asn Phe Thr Asp Tyr Ser
145                 150                 155                 160

Ser Ser Ser Leu Glu Gln Phe Trp Asn Asp Trp Val Gly Val Glu
                165                 170                 175

Glu Pro Pro Phe Ala Tyr Val Pro Glu Pro Pro Asn Pro Tyr Pro Leu
            180                 185                 190

Pro Asn Ala Pro Pro Ile Tyr Pro Glu Tyr Tyr Thr Lys Arg Pro
            195                 200                 205

Lys Asp Ile Leu Pro Asp Tyr Lys Phe Pro Lys Asp Phe Leu Phe Gly
    210                 215                 220

Trp Ala Thr Ala Ala Gln Gln Trp Glu Gly Ala Val Lys Ala Asp Gly
225                 230                 235                 240

Lys Gly Pro Ser Ile Trp Asp Trp Ala Ser Arg Phe Pro Gly Phe Ile
                245                 250                 255

Ala Asp Asn Thr Thr Ser Asp Val Gly Asp Leu Gly Tyr Tyr Leu Tyr
            260                 265                 270

Lys Glu Asp Leu Ala Arg Ile Ala Ala Leu Gly Ala Asn Val Tyr Ser
    275                 280                 285

Phe Ser Met Phe Trp Thr Arg Ile Phe Pro Phe Gly Lys Ala Asp Ser
```

```
              290                 295                 300
Pro Val Asn Gln Ala Gly Ile Asp Phe Tyr His Asp Leu Ile Asp Tyr
305                 310                 315                 320

Ser Trp Ser Leu Gly Ile Glu Pro Val Val Thr Leu Phe His Trp Asp
                    325                 330                 335

Thr Pro Leu Ala Leu Gln Leu Glu Tyr Gly Gly Phe Ala Ser Glu Arg
                340                 345                 350

Ile Ile Asp Asp Tyr Val Asn Tyr Ala Glu Thr Val Phe Lys Ala Tyr
            355                 360                 365

Asn Gly Ser Val His Lys Trp Val Thr Phe Asn Glu Pro Val Val Phe
        370                 375                 380

Cys Ser Gln Met Ala Ala Pro Val Asn Thr Thr Leu Pro Pro Asn Leu
385                 390                 395                 400

Asn Ser Thr Ile Tyr Pro Tyr Thr Cys Ser Tyr His Leu Val Leu Ala
                    405                 410                 415

His Ala Lys Thr Val Lys Arg Phe Arg Glu Leu Asn Ile Gln Gly Gln
                420                 425                 430

Ile Ala Phe Lys Ser Asp Asn Phe Val Gly Ile Pro Trp Arg Glu Gly
            435                 440                 445

Asn Gln Glu Asp Ile Asp Ala Val Glu Arg His Gln Ala Tyr Gln Ile
        450                 455                 460

Gly Ile Phe Ala Glu Pro Ile Tyr Asn Thr Gly Asp Trp Pro Asp Ile
465                 470                 475                 480

Val Lys Asn Asp Leu Ser Pro Asp Ile Leu Pro Arg Phe Thr Asp Asp
                    485                 490                 495

Glu Ile Ala Met Ile Lys Cys Thr Ala Asp Phe Phe Pro Ile Asp Gly
                500                 505                 510

Tyr Arg Asp Gly Tyr Val Gln Ala Val Pro Gly Gly Val Glu Ala Cys
            515                 520                 525

Val Ala Asn Ile Ser Asn Pro Leu Trp Pro Ala Cys Asn Gln Val Asn
        530                 535                 540

Phe Tyr Asp Ser Thr Pro Ala Gly Trp Ala Ile Gly Thr Phe Gly Asn
545                 550                 555                 560

Trp Pro Thr Thr Pro Trp Leu Gln Asn Thr Trp Gln Phe Val Arg Pro
                    565                 570                 575

Phe Leu Ala Asp Leu Ala Lys Arg Tyr Pro Thr Glu Gly Gly Ile Tyr
                580                 585                 590

Leu Ser Glu Phe Gly Phe Ser Glu Pro Phe Glu Asn Asp Lys Thr Phe
            595                 600                 605

Ile Tyr Gln Ile Thr Gln Asp Ser Gly Arg Thr Ala Tyr Phe Asn Ser
        610                 615                 620

Tyr Leu Gly Glu Val Leu Lys Gly Ile Val Glu Asp Gly Ile Pro Ile
625                 630                 635                 640

Lys Gly Val Phe Gly Trp Ser Met Val Asp Asn Phe Glu Trp Asn Ser
                    645                 650                 655

Gly Leu Ser Thr Arg Phe Gly Val Gln Tyr Val Asp Tyr Asn Ser Pro
                660                 665                 670

Thr Arg Gln Arg Thr Phe Lys Arg Ser Ala Leu Glu Met Ser Glu Phe
            675                 680                 685

Trp Asn Ala His Arg Cys Ser Ala
        690                 695

<210> SEQ ID NO 2
```

<211> LENGTH: 566
<212> TYPE: PRT
<213> ORGANISM: Cryptococcus terrestris

<400> SEQUENCE: 2

```
Ala Thr Thr Asn Gln Asp Ala Ile Thr Pro Thr Ala Thr Gly Pro Val
1               5                   10                  15

Gly Gly Gln Gly Thr Pro Ala Val Asn Phe Thr Asp Tyr Ser Ser Ser
            20                  25                  30

Ser Leu Glu Gln Phe Trp Asn Asp Trp Val Gly Glu Val Glu Glu Pro
        35                  40                  45

Pro Phe Ala Tyr Val Pro Glu Pro Pro Asn Pro Tyr Pro Leu Pro Asn
    50                  55                  60

Ala Pro Pro Pro Ile Tyr Pro Glu Tyr Tyr Thr Lys Arg Pro Lys Asp
65                  70                  75                  80

Ile Leu Pro Asp Tyr Lys Phe Pro Lys Asp Phe Leu Phe Gly Trp Ala
                85                  90                  95

Thr Ala Ala Gln Gln Trp Glu Gly Ala Val Lys Ala Asp Gly Lys Gly
            100                 105                 110

Pro Ser Ile Trp Asp Trp Ala Ser Arg Phe Pro Gly Phe Ile Ala Asp
        115                 120                 125

Asn Thr Thr Ser Asp Val Gly Asp Leu Gly Tyr Tyr Leu Tyr Lys Glu
    130                 135                 140

Asp Leu Ala Arg Ile Ala Ala Leu Gly Ala Asn Val Tyr Ser Phe Ser
145                 150                 155                 160

Met Phe Trp Thr Arg Ile Phe Pro Phe Gly Lys Ala Asp Ser Pro Val
                165                 170                 175

Asn Gln Ala Gly Ile Asp Phe Tyr His Asp Leu Ile Asp Tyr Ser Trp
            180                 185                 190

Ser Leu Gly Ile Glu Pro Val Val Thr Leu Phe His Trp Asp Thr Pro
        195                 200                 205

Leu Ala Leu Gln Leu Glu Tyr Gly Gly Phe Ala Ser Glu Arg Ile Ile
    210                 215                 220

Asp Asp Tyr Val Asn Tyr Ala Glu Thr Val Phe Lys Ala Tyr Asn Gly
225                 230                 235                 240

Ser Val His Lys Trp Val Thr Phe Asn Glu Pro Val Val Phe Cys Ser
                245                 250                 255

Gln Met Ala Ala Pro Val Asn Thr Thr Leu Pro Pro Asn Leu Asn Ser
            260                 265                 270

Thr Ile Tyr Pro Tyr Thr Cys Ser Tyr His Leu Val Leu Ala His Ala
        275                 280                 285

Lys Thr Val Lys Arg Phe Arg Glu Leu Asn Ile Gln Gly Gln Ile Ala
    290                 295                 300

Phe Lys Ser Asp Asn Phe Val Gly Ile Pro Trp Arg Glu Gly Asn Gln
305                 310                 315                 320

Glu Asp Ile Asp Ala Val Glu Arg His Gln Ala Tyr Gln Ile Gly Ile
                325                 330                 335

Phe Ala Glu Pro Ile Tyr Asn Thr Gly Asp Trp Pro Asp Ile Val Lys
            340                 345                 350

Asn Asp Leu Ser Pro Asp Ile Leu Pro Arg Phe Thr Asp Glu Ile
        355                 360                 365

Ala Met Ile Lys Cys Thr Ala Asp Phe Phe Pro Ile Asp Gly Tyr Arg
    370                 375                 380

Asp Gly Tyr Val Gln Ala Val Pro Gly Gly Val Glu Ala Cys Val Ala
```

```
                385                 390                 395                 400
        Asn Ile Ser Asn Pro Leu Trp Pro Ala Cys Asn Gln Val Asn Phe Tyr
                        405                 410                 415

Asp Ser Thr Pro Ala Gly Trp Ala Ile Gly Thr Phe Gly Asn Trp Pro
                        420                 425                 430

Thr Thr Pro Trp Leu Gln Asn Thr Trp Gln Phe Val Arg Pro Phe Leu
                        435                 440                 445

Ala Asp Leu Ala Lys Arg Tyr Pro Thr Glu Gly Ile Tyr Leu Ser
                450                 455                 460

Glu Phe Gly Phe Ser Glu Pro Phe Glu Asn Asp Lys Thr Phe Ile Tyr
        465                 470                 475                 480

Gln Ile Thr Gln Asp Ser Gly Arg Thr Ala Tyr Phe Asn Ser Tyr Leu
                        485                 490                 495

Gly Glu Val Leu Lys Gly Ile Val Glu Asp Gly Ile Pro Ile Lys Gly
                        500                 505                 510

Val Phe Gly Trp Ser Met Val Asp Asn Phe Glu Trp Asn Ser Gly Leu
                        515                 520                 525

Ser Thr Arg Phe Gly Val Gln Tyr Val Asp Tyr Asn Ser Pro Thr Arg
                530                 535                 540

Gln Arg Thr Phe Lys Arg Ser Ala Leu Glu Met Ser Glu Phe Trp Asn
        545                 550                 555                 560

Ala His Arg Cys Ser Ala
                        565

<210> SEQ ID NO 3
<211> LENGTH: 560
<212> TYPE: PRT
<213> ORGANISM: Cryptococcus terrestris

<400> SEQUENCE: 3

Ala Ile Thr Pro Thr Ala Thr Gly Pro Val Gly Gly Gln Gly Thr Pro
        1               5                   10                  15

Ala Val Asn Phe Thr Asp Tyr Ser Ser Ser Leu Glu Gln Phe Trp
                        20                  25                  30

Asn Asp Trp Val Gly Glu Val Glu Pro Phe Ala Tyr Val Pro
                        35                  40                  45

Glu Pro Pro Asn Pro Tyr Pro Leu Pro Asn Ala Pro Pro Ile Tyr
        50                  55                  60

Pro Glu Tyr Tyr Thr Lys Arg Pro Lys Asp Ile Leu Pro Asp Tyr Lys
        65                  70                  75                  80

Phe Pro Lys Asp Phe Leu Phe Gly Trp Ala Thr Ala Ala Gln Gln Trp
                        85                  90                  95

Glu Gly Ala Val Lys Ala Asp Gly Lys Gly Pro Ser Ile Trp Asp Trp
                        100                 105                 110

Ala Ser Arg Phe Pro Gly Phe Ile Ala Asp Asn Thr Thr Ser Asp Val
                        115                 120                 125

Gly Asp Leu Gly Tyr Tyr Leu Tyr Lys Glu Asp Leu Ala Arg Ile Ala
                130                 135                 140

Ala Leu Gly Ala Asn Val Tyr Ser Phe Ser Met Phe Trp Thr Arg Ile
        145                 150                 155                 160

Phe Pro Phe Gly Lys Ala Asp Ser Pro Val Asn Gln Ala Gly Ile Asp
                        165                 170                 175

Phe Tyr His Asp Leu Ile Asp Tyr Ser Trp Ser Leu Gly Ile Glu Pro
                        180                 185                 190
```

```
Val Val Thr Leu Phe His Trp Asp Thr Pro Leu Ala Leu Gln Leu Glu
        195                 200                 205

Tyr Gly Gly Phe Ala Ser Glu Arg Ile Ile Asp Asp Tyr Val Asn Tyr
210                 215                 220

Ala Glu Thr Val Phe Lys Ala Tyr Asn Gly Ser Val His Lys Trp Val
225                 230                 235                 240

Thr Phe Asn Glu Pro Val Val Phe Cys Ser Gln Met Ala Ala Pro Val
                245                 250                 255

Asn Thr Thr Leu Pro Pro Asn Leu Asn Ser Thr Ile Tyr Pro Tyr Thr
            260                 265                 270

Cys Ser Tyr His Leu Val Leu Ala His Ala Lys Thr Val Lys Arg Phe
        275                 280                 285

Arg Glu Leu Asn Ile Gln Gly Gln Ile Ala Phe Lys Ser Asp Asn Phe
290                 295                 300

Val Gly Ile Pro Trp Arg Glu Gly Asn Gln Glu Asp Ile Asp Ala Val
305                 310                 315                 320

Glu Arg His Gln Ala Tyr Gln Ile Gly Ile Phe Ala Glu Pro Ile Tyr
                325                 330                 335

Asn Thr Gly Asp Trp Pro Asp Ile Val Lys Asn Asp Leu Ser Pro Asp
            340                 345                 350

Ile Leu Pro Arg Phe Thr Asp Glu Ile Ala Met Ile Lys Cys Thr
        355                 360                 365

Ala Asp Phe Phe Pro Ile Asp Gly Tyr Arg Asp Gly Tyr Val Gln Ala
370                 375                 380

Val Pro Gly Gly Val Glu Ala Cys Val Ala Asn Ile Ser Asn Pro Leu
385                 390                 395                 400

Trp Pro Ala Cys Asn Gln Val Asn Phe Tyr Asp Ser Thr Pro Ala Gly
                405                 410                 415

Trp Ala Ile Gly Thr Phe Gly Asn Trp Pro Thr Thr Pro Trp Leu Gln
            420                 425                 430

Asn Thr Trp Gln Phe Val Arg Pro Phe Leu Ala Asp Leu Ala Lys Arg
        435                 440                 445

Tyr Pro Thr Glu Gly Gly Ile Tyr Leu Ser Glu Phe Gly Phe Ser Glu
450                 455                 460

Pro Phe Glu Asn Asp Lys Thr Phe Ile Tyr Gln Ile Thr Gln Asp Ser
465                 470                 475                 480

Gly Arg Thr Ala Tyr Phe Asn Ser Tyr Leu Gly Glu Val Leu Lys Gly
                485                 490                 495

Ile Val Glu Asp Gly Ile Pro Lys Gly Val Phe Gly Trp Ser Met
            500                 505                 510

Val Asp Asn Phe Glu Trp Asn Ser Gly Leu Ser Thr Arg Phe Gly Val
        515                 520                 525

Gln Tyr Val Asp Tyr Asn Ser Pro Thr Arg Gln Arg Thr Phe Lys Arg
530                 535                 540

Ser Ala Leu Glu Met Ser Glu Phe Trp Asn Ala His Arg Cys Ser Ala
545                 550                 555                 560

<210> SEQ ID NO 4
<211> LENGTH: 555
<212> TYPE: PRT
<213> ORGANISM: Cryptococcus terrestris

<400> SEQUENCE: 4

Ala Thr Gly Pro Val Gly Gly Gln Gly Thr Pro Ala Val Asn Phe Thr
1               5                   10                  15
```

-continued

Asp Tyr Ser Ser Ser Leu Glu Gln Phe Trp Asn Asp Trp Val Gly
            20              25              30

Glu Val Glu Glu Pro Pro Phe Ala Tyr Val Pro Glu Pro Asn Pro
        35              40              45

Tyr Pro Leu Pro Asn Ala Pro Pro Ile Tyr Pro Glu Tyr Tyr Thr
    50              55              60

Lys Arg Pro Lys Asp Ile Leu Pro Asp Tyr Lys Phe Pro Lys Asp Phe
65              70              75              80

Leu Phe Gly Trp Ala Thr Ala Ala Gln Gln Trp Glu Gly Ala Val Lys
                85              90              95

Ala Asp Gly Lys Gly Pro Ser Ile Trp Asp Trp Ala Ser Arg Phe Pro
            100             105             110

Gly Phe Ile Ala Asp Asn Thr Thr Ser Asp Val Gly Asp Leu Gly Tyr
            115             120             125

Tyr Leu Tyr Lys Glu Asp Leu Ala Arg Ile Ala Ala Leu Gly Ala Asn
130             135             140

Val Tyr Ser Phe Ser Met Phe Trp Thr Arg Ile Phe Pro Phe Gly Lys
145             150             155             160

Ala Asp Ser Pro Val Asn Gln Ala Gly Ile Asp Phe Tyr His Asp Leu
            165             170             175

Ile Asp Tyr Ser Trp Ser Leu Gly Ile Glu Pro Val Val Thr Leu Phe
            180             185             190

His Trp Asp Thr Pro Leu Ala Leu Gln Leu Glu Tyr Gly Gly Phe Ala
            195             200             205

Ser Glu Arg Ile Ile Asp Asp Tyr Val Asn Tyr Ala Glu Thr Val Phe
            210             215             220

Lys Ala Tyr Asn Gly Ser Val His Lys Trp Val Thr Phe Asn Glu Pro
225             230             235             240

Val Val Phe Cys Ser Gln Met Ala Ala Pro Val Asn Thr Thr Leu Pro
            245             250             255

Pro Asn Leu Asn Ser Thr Ile Tyr Pro Tyr Thr Cys Ser Tyr His Leu
            260             265             270

Val Leu Ala His Ala Lys Thr Val Lys Arg Phe Arg Glu Leu Asn Ile
            275             280             285

Gln Gly Gln Ile Ala Phe Lys Ser Asp Asn Phe Val Gly Ile Pro Trp
            290             295             300

Arg Glu Gly Asn Gln Glu Asp Ile Asp Ala Val Glu Arg His Gln Ala
305             310             315             320

Tyr Gln Ile Gly Ile Phe Ala Glu Pro Ile Tyr Asn Thr Gly Asp Trp
            325             330             335

Pro Asp Ile Val Lys Asn Asp Leu Ser Pro Asp Ile Leu Pro Arg Phe
            340             345             350

Thr Asp Asp Glu Ile Ala Met Ile Lys Cys Thr Ala Asp Phe Phe Pro
            355             360             365

Ile Asp Gly Tyr Arg Asp Gly Tyr Val Gln Ala Val Pro Gly Gly Val
            370             375             380

Glu Ala Cys Val Ala Asn Ile Ser Asn Pro Leu Trp Pro Ala Cys Asn
385             390             395             400

Gln Val Asn Phe Tyr Asp Ser Thr Pro Ala Gly Trp Ala Ile Gly Thr
            405             410             415

Phe Gly Asn Trp Pro Thr Thr Pro Trp Leu Gln Asn Thr Trp Gln Phe
            420             425             430

-continued

```
Val Arg Pro Phe Leu Ala Asp Leu Ala Lys Arg Tyr Pro Thr Glu Gly
    435             440             445

Gly Ile Tyr Leu Ser Glu Phe Gly Phe Ser Glu Pro Phe Glu Asn Asp
    450             455             460

Lys Thr Phe Ile Tyr Gln Ile Thr Gln Asp Ser Gly Arg Thr Ala Tyr
465             470             475             480

Phe Asn Ser Tyr Leu Gly Glu Val Leu Lys Gly Ile Val Glu Asp Gly
            485             490             495

Ile Pro Ile Lys Gly Val Phe Gly Trp Ser Met Val Asp Asn Phe Glu
            500             505             510

Trp Asn Ser Gly Leu Ser Thr Arg Phe Gly Val Gln Tyr Val Asp Tyr
    515             520             525

Asn Ser Pro Thr Arg Gln Arg Thr Phe Lys Arg Ser Ala Leu Glu Met
    530             535             540

Ser Glu Phe Trp Asn Ala His Arg Cys Ser Ala
545             550             555
```

METHOD FOR PREPARING GALACTO-OLIGOSACHARIDES FROM LACTULOSE

CROSS REFERENCE TO RELATED APPLICATIONS

This application is a U.S. national phase application of International Application No. PCT/EP2020/084190, filed Dec. 2, 2020, which claims benefit from European Application 19213166.2, filed Dec. 3, 2019, which are each hereby incorporated herein by reference in their entirety.

FIELD

The present invention relates to the preparation of galacto-oligosaccharides (GOS) acceptable to subjects suffering from GOS-related allergy and subjects having lactose intolerance.

BACKGROUND

Conventional GOS comprises a chain of galactose units and a terminal glucose unit, that arises through consecutive transgalactosylation reactions, catalyzed by a beta-galactosidase. Some of the GOS components exist naturally in human breast milk and bovine colostrum. Typical GOS preparations mainly comprise di- to hexa-saccharides.

Various physiological functions of GOS have been reported, including the capacity to stimulate the growth of bifidogenic bacteria in the gut, to support normal gut transit, to contribute to natural defenses, to enhance mineral absorption, and to stimulate immune functions and lower inflammations. GOS has received particular attention for its pre-biotic effects that promote the growth of *Bifidobacterium*, *Lactobacillus*, and other enteric bacteria. Therefore, GOS is commonly used in infant formula, beverages fermented by *Lactobacillus*, yogurts, juices and drinks. Some of these GOS-containing foods are certified as Food for Specified Health Uses by the Consumer Affairs Agency in Japan, and GOS is certified as Generally Recognized As Safe (GRAS) substances by the U.S. Food and Drug Administration (GRAS Notices: GRN 233, 236, 285, 286, 334, 484, 489, 495, 518, and 569).

GOS is conventionally made by contacting a lactose-containing feed with a beta-galactosidase. The resulting GOS is a mixture of galacto-oligosaccharides with different degrees of polymerization (DP), including lactose. A large part of the world-wide population above 3 years of age suffers from lactose intolerance, which may result in abdominal pain, bloating, diarrhea, gas, and nausea upon consumption of lactose-containing compositions. Conventional GOS contains lactose and thus may cause these symptoms.

Therefore, a need exists to produce a GOS that does not contain lactose. Solving this problem by removing lactose from conventional GOS is not a viable option because the removal of lactose requires the use of a lactose-hydrolyzing enzyme—lactase—that will not only hydrolyse lactose but also other GOS components, resulting in the loss of GOS functionalities.

The beta-galctosidase enzymes that are used for the production of conventional GOS are those produced in many microorganisms such as *Bacillus circulans, Aspergillus oryzae, Kluyveromyces marxianus, Kluyveromyces fragilis, Sporobolomyces singularis*, and *Lactobacillus fermentum*. Beta-galactosidases differ in their three-dimensional structures, resulting in stereo- and regioselective formation of the glycosidic bonds. For example, a fungal beta-galactosidase derived from *Aspergillus* predominantly produces (β1-6 bonds (thus resulting in a GOS preparation that predominantly comprises (β1-6 bonds, which may be referred to as "6'-GOS"), while a bacterial beta-galactosidase derived from *Bacillus circulans* predominantly produce (β1-4 bonds (resulting in a GOS preparation that predominantly comprises (β1-4 bonds, which may also be referred to as "4'-GOS"). Moreover, beta-galactosidase produced by *B. circulans* possesses particularly strong transgalactosylation activity. As a result, GOS prepared by *B. circulans* is sold worldwide.

Since its introduction to the market (1999), approximately more than 100 million of infants have consumed infant formula containing GOS prepared by *B. circulans*. It has been proven to be a safe ingredient, with a GRAS status acknowledged by the FDA. In the past few years, however, a small number of very rare cases of GOS-related allergy (~2 per million) has been reported in South East Asia. Research has shown that certain oligosaccharide structures present in GOS can exert an allergic response in very sensitive subjects.

DETAILED DESCRIPTION

The object of the present invention is therefore to provide a GOS preparation that is well tolerated by subjects suffering from lactose intolerance and by subjects suffering from allergic responses to conventional GOS obtained by *Bacillus circulans* beta-galactosidase or *Aspergillus oryzae* beta-galactosidase.

This object has been met by the present invention, which involves the production of a GOS preparation by contacting a lactulose-containing feed with β-galactosidase derived from the microorganism *Papiliotrema terrestris*.

A previous name of the microorganism "*Papiliotrema terrestris*" is "*Cryptococcus Papiliotrema terrestris*". The names "*Cryptococcus terrestris*" (*C. terrestris*) and "*Papiliotrema terrestris*" (*P. terrestris*) thus refer to the same organism.

By "β-galactosidase derived from *P. terrestris*" is meant a β-galactosidase enzyme produced by a microorganism (of either a wild-type strain or a mutant strain) which is classified into *Papiliotrema terrestris*, or a β-galactosidase enzyme obtained by genetic engineering procedures using the β-galactosidase gene from a microorganism (of either a wild-type strain or a mutant strain) which is classified into *Papiliotrema terrestris*. Therefore, the term "β-galactosidase derived from *Papiliotrema terrestris*" also encompasses a recombinant enzyme that is produced by a host microorganism into which the β-galactosidase gene (or a modified gene thereof) obtained from *Papiliotrema terrestris* has been introduced.

The resulting GOS preparation differs from conventional GOS, which is made from lactose, in that it has a fructose instead of a glucose residue at the reducing end. We therefore also refer to this lactulose-derived GOS as fGOS.

This fGOS is clinically lactose-free, meaning that the ratio oligosaccharides other than lactose to lactose is at least 10. Preferably, the fGOS obtained by the process of the present invention is essentially free of lactose, meaning that it does not contain more than traces—i.e. not more than 1 wt %, preferably not more than 0.5 wt %, and most preferably not more than 0.1 wt %, based on dry matter—of lactose. In a most preferred embodiment, the fGOS obtained according to the present invention does not contain any lactose.

Furthermore, the process according to the present invention allows to obtain an fGOS preparation that—without any purification or concentration steps to remove lactulose or monosugars—contains, based on dry matter, 30-60 wt %, preferably 40-60 wt % of galacto-oligosaccharide. This content of oligosaccharide does not include lactulose, but does include DP2 oligosaccharides other than lactulose. The other ingredients of this fGOS preparation mainly consist of lactulose and monosugars (fructose, galactose, glucose).

The production of GOS from lactulose is known from the prior art. For instance, C. Guerrero et al., *Food Chemistry* 138 (2013) 2225-2232, discloses the production of GOS from lactose and lactulose using β-galactosidases derived from three different sources. It was found that the GOS yield from lactulose was highest with *Aspergillus oryzae*-derived beta-galactosidase and lowest with *Bacillus circulans*-derived beta-galactosidase. The reverse order was found when starting from lactose: highest yield was obtained with *Bacillus circulans*-derived beta-galactosidase; lowest yield with *Aspergillus oryzae*-derived beta-galactosidase.

As shown in the Examples below, it has now been found that *P. terrestris*-derived beta-galactosidase is even better suited for GOS production from lactulose than *Aspergillus oryzae*-derived beta-galactosidase.

Furthermore, the fGOS preparation obtained with the process of the present invention has a reduced (IgE-mediated) allergic response in a subject. In other words: this fGOS preparation, when administered to a subject suffering from at least one type of GOS-related allergy, i.e. an allergy caused by GOS produced by *Bacillus circulans*-derived beta-galactosidase and/or by GOS produced by *Aspergillus oryzae*-derived beta-galactosidase, evokes a reduced allergic response when compared to a GOS preparation produced by *Bacillus circulans* or *Aspergillus oryzae*-derived beta-galactosidase. More in particular, the fGOS preparation according to the present invention has a decreased score in a Skin Prick Test in the subject and/or in a Basophil Activation Test performed on a blood sample isolated from the subject when compared to a GOS preparation obtained by *Bacillus circulans* or *Aspergillus oryzae* derived beta-galactosidase.

And since the fGOS preparation is clinically lactose free, it is also tolerated well by subjects suffering from lactose intolerance.

The invention therefore also relates to a method for at least partially preventing hypersensitivity to a GOS preparation in a subject, comprising administering to said subject the fGOS preparation according to the present invention or a nutritional composition comprising said fGOS preparation.

The subject is a mammal, in particular a human being. Although the subject may have any age, the subject is preferably aged at least 18 months, preferably at least 24 months, even more preferably at least 3 years (36 months), and most preferably at least 13 years.

The rare GOS-related allergy has not been reported in subjects having an age of 18 months or below and lactose intolerance generally does not occur below the age of 2 years.

In view of the localized incidence of the 4'-GOS and/or 6'-GOS-related allergies in South East Asia (e.g. Singapore, Japan) and the abundant lactose intolerance within the Asian population, the subject is preferably of (South East) Asian origin.

The β-galactosidase enzyme used for the manufacture of the fGOS preparation is known per se from patent application US 2019-119662 (originating from. PCT/JP2016/089001).

In WO2019/002304, the use of this enzyme for the production of hypoallergenic GOS is disclosed. Said hypoallergenic GOS is obtained from a conventional lactose feed and may therefore cause health issues in lactose intolerant subjects.

The fGOS preparation can be administered to a subject in the form of a nutritional composition. Such nutritional composition comprises (i) the fGOS preparation obtainable by the process of the present invention and (ii) at least one further ingredient selected from the group consisting of protein sources, probiotics, lipid sources, and carbohydrates.

As used herein, a nutritional composition refers to any composition or formulation that goes into the alimentary canal for nutritional purposes, in whatever solid, liquid, or gaseous state. Thus, a nutritional composition can be a food item or a drink item. Examples of nutritional compositions according to the present invention are infant formula, Growing Up Milk (GUM), beverages fermented by *Lactobacillus*, yogurts, food supplements, and nutritional fortifiers.

Examples of protein sources that may be present in the nutritional composition include whey proteins (e.g. whey protein concentrate or whey protein isolate), casein (e.g. micellar casein isolate), milk protein concentrate or isolate, and/or plant proteins such as soy protein. In a preferred embodiment, the protein source is a hypoallergenic or non-allergenic protein source. This includes protein hydrolysates that can be administered to subjects having intolerance against dietary proteins, more particularly cow's milk proteins, without inducing allergic reactions. Examples of such protein hydrolysates are hydrolyzed whey proteins containing hydrolysis residues having a molecular weight below 10,000 Da and casein hydrolysate with peptides of maximally 3000 Da.

Examples of carbohydrate sources that may be present in the nutritional composition are disaccharides such as saccharose, monosaccharides, such as glucose, and maltodextrins, starch and carbohydrate sources having a prebiotic effect. The presence of lactose is evidently undesired.

Examples of lipid sources that may be present in the nutritional composition are tri-, di-, and monoglycerides, phospholipids, sphingolipids, fatty acids, and esters or salts thereof. The lipids may have an animal, vegetable, microbial or synthetic origin. Of particular interest are polyunsaturated fatty acids (PUFAs) such as gamma linolenic acid (GLA), dihomo gamma linolenic acid (DHGLA), arachidonic acid (AA), stearidonic acid (SA), eicosapentaenoic acid (EPA), docosahexaenoic acid (DHA), docosapentaenoic acid (DPA) and conjugated linoleic acid (CLA). CLA is important in the protection against eczema and respiratory diseases in children. This particularly involves the cis-9, trans-11 and cis-12 isomers of CLA. Examples of suitable vegetable lipid sources include sun flower oil, high oleic sun flower oil, coconut oil, palm oil, palm kernel oil, soy bean oil, etc. Examples of suitable lipid sources of animal origin include milkfat, for example anhydrous milkfat (AMF), cream, etc. In a preferred embodiment, a combination of milkfat and lipids of vegetable origin are used.

The nutritional composition may further comprise a probiotic. In the context of the present invention, the term "probiotic" refers to a strain of probiotic bacteria. Probiotic bacteria are known in the art. Suitably, the probiotic bacteria are not genetically modified. Suitable probiotic bacteria include bacteria of the genus Bifidobacteria (e.g. *B. breve, B. longum, B. infantis, B. bifidum*), *Lactobacillus* (e.g. *L. Acidophilus, L. paracasei, L. johnsonii, L. plantarum, L. reuteri, L. rhamnosus, L. casei, L. lactis*), and *Streptococcus* (e.g. *S. thermophilus*). *B. breve* and *B. longum* are especially suitable probiotics. Suitable *B. breve* strains may for example be isolated from the faeces of healthy human milk-fed infants. The combination of a prebiotic and a probiotic is also referred to as a "synbiotic". The probiotic may be present in the composition at any suitable concentration, suitably in a therapeutically effective amount or "amount effective for treating" in the context of the invention. Suitably, the probiotic is included in the present composition in an amount of $10^2$-$10e^{13}$ cfu per g dry weight of the composition, suitably $10^5$-$10^{12}$ cfu/g, most suitably $10^7$-$10^{10}$ cfu/g.

Further, the nutritional composition may contain one or more conventional micro ingredients, such as vitamins, antioxidants, minerals, free amino acids, nucleotides, taurine, carnitine and polyamines. Examples of suitable antioxidants are BHT, ascorbyl palmitate, vitamin E, alpha and beta carotene, lutein, zeaxanthin, lycopene and phospholipids.

The β-galactosidase used in the process of the present invention has been disclosed extensively in WO2019/002304. It may be obtained from the *Papiliotrema terrestris* strain MM13-F2171 or from its mutant strains M2 and M6. Mutant strains (M2 and M6) can be obtained from *Papiliotrema terrestris* strain MM13-F2171 by means of mutagenesis with UV treatment. *Papiliotrema terrestris* strains MM13-F2171 and M2 have been deposited at a depository, as described below, and are readily available.

<*Papiliotrema terrestris* Strain MM13-F2171>
  Depository: Patent Microorganisms Depositary, National Institute of Technology and Evaluation (Room 122, 2-5-8 Kazusa Kamatari, Kisarazu-shi, Chiba, 292-0818, JAPAN). Identification reference: *Cryptococcus terrestris* MM13-F2171. Date of deposit: Dec. 10, 2015. Accession number: NITE BP-02177;

<*Papiliotrema terrestris* Strain M2>
  Depository: Patent Microorganisms Depositary, National Institute of Technology and Evaluation (Room 122, 2-5-8 Kazusa Kamatari, Kisarazu-shi, Chiba, 292-0818, JAPAN). Identification reference: *Cryptococcus terrestris* APC-6431. Date of deposit: Dec. 10, 2015. Accession number: NITE BP-02178

Accordingly, in one embodiment the enzyme used in the present invention is derived from *Papiliotrema terrestris* strain MM13-F2171 (Accession Number: NITE BP-02177) or APC-6431 (Accession Number: NITE BP-02178).

In a further embodiment, the enzyme comprises an amino acid sequence according to any of SEQ ID NO: 1, 2, 3 or 4, or an amino acid sequence that is at least 80%, preferably at least 85%, more preferably at least 90%, even more preferably at least 95%, yet even more preferably at least 97%, and most preferably at least 99% identical to any of SEQ ID NO: 1, 2, 3 or 4.

US 2019-119662 describes three kinds of β-galactosidase produced by mutant strains derived from the *Papiliotrema* microorganism (mutant strain enzymes 1, 2, and 3), and determined their amino acid sequences. These three β-galactosidase enzymes were found to have a partial sequence of the full-length amino acid sequence of the wild-type strain enzyme (the wild-type strain enzyme is shown in SEQ ID NO: 1), which is deduced from its gene sequence. Specifically, these mutant enzymes are one having an amino acid sequence in which the N-terminal 130 amino acid residues of the full-length amino acid sequence of the wild-type strain enzyme are deleted, which is referred to as "mutant strain enzyme 1" for the purpose of description (see SEQ ID NO: 2); one having an amino acid sequence in which the N-terminal 136 amino acid residues of the full-length amino acid sequence of the wild-type strain enzyme are deleted (see SEQ ID NO:3), which is referred to as "mutant strain enzyme 2" for the purpose of description; and one having an amino acid sequence in which the N-terminal 141 amino acid residues of the full-length amino acid sequence of the wild-type strain enzyme are deleted (see SEQ ID NO:4), which is referred to as "mutant strain enzyme 3".

The term "equivalent amino acid sequence" in this case means an amino acid sequence which is partially different from the reference amino acid sequence (i.e. amino acid sequence of any one of SEQ ID NOs:1 to 4), but the difference does not substantially influence the function of the protein (beta-galactosidase activity). Thus, an enzyme having a polypeptide chain of the equivalent amino acid sequence shows a beta-galactosidase activity.

The term "partial difference in the amino acid sequence" typically means mutation (change) in the amino acid sequence caused by deletion or substitution of one to several (up to, for example, 3, 5, 7, or 10) amino acids composing the amino acid sequence, or addition, insertion, or a combination thereof of one to several (up to, for example, 3, 5, 7, or 10) amino acids. The difference in the amino acid sequence is acceptable as long as the beta-galactosidase activity is maintained (the activity may be varied to a degree). As long as the conditions are satisfied, the position of the difference in the amino acid sequence is not particularly limited, and the difference may arise in a plurality of positions. The term "plurality" means, for example, a number corresponding to less than about 20%, preferably less than about 15%, more preferably less than about 10%, even more preferably less than about 5% of the total amino acids, and most preferably less than about 1%. More specifically, the equivalent protein has, for example, about 80% or more, preferably about 85% or more, more preferably about 90% or more, much more preferably about 95% or more, even more preferably about 97% or more, and most preferably about 99% or more identity with the reference amino acid sequence.

The difference of the amino acid sequence may arise in a plurality of positions. Preferably, the equivalence protein is obtained by causing conservative amino acid substitution in an amino acid residue which is not essential for beta-galactosidase activity. The term "conservative amino acid substitution" means the substitution of an amino acid residue with another amino acid residue having a side chain with similar properties.

Amino acid residues are classified into several families according to their side chains, such as basic side chains (for example, lysine, arginine, and histidine), acidic side chains (for example, aspartic acid and glutamic acid), uncharged polar side chains (for example, glycine, asparagine, glutamine, serine, threonine, tyrosine, and cysteine), nonpolar side chains (for example, alanine, valine, leucine, isoleucine, proline, phenylalanine, methionine, and tryptophan), β-branched side chains (for example, threonine, valine, and isoleucine), and aromatic side chains (for example, tyrosine, phenylalanine, tryptophan, and histidine). Conservative amino acid substitution is preferably the substitution between amino acid residues in one family.

The identity (%) between two amino acid sequences or two nucleic acid sequences (hereinafter, the term "two sequences" are used for representing either of two sequences) can be determined by the following procedure. Firstly, two sequences are aligned for optimum comparison of the two sequences (for example, a gap may be introduced into the first sequence so as to optimize the alignment with respect to the second sequence). When a molecule (amino acid residue or nucleotide) at a specific position in the first sequence and a molecule in the corresponding position in the second sequence are the same as each other, the molecules in the positions are defined as being identical. The identity between two sequences is a function of the number of identical positions shared by the two sequences (i.e., identity (%)=100*number of identical positions/total number of positions). Preferably, the number and size of the gaps, which are required to optimize the alignment of the two sequences, are taken into consideration. For further information concerning the determination of the identity between two sequences, it is referred to WO 2019/002304, page 17, line 11 through page 18, line 7.

An enzyme for use in the process of the present invention having the above-described amino acid sequence may also be prepared by a genetic engineering technique. For example, an appropriate host cell (for example, *Escherichia coli*) is transformed by a DNA encoding the present enzyme, and the protein expressed in the transformant is collected, and thereby preparing the present enzyme. The collected protein is treated as appropriate according to the intended use. The enzyme thus obtained as a recombinant protein may be subjected to various modifications. For example, the enzyme composed of a recombinant protein linked to any peptide or protein can be obtained by producing a recombinant protein using a vector into which a DNA encoding the enzyme has been inserted together with other appropriate DNA. In addition, modification for causing addition of a sugar chain and/or a lipid, or N- or C-terminal processing may be carried out. These modifications allow, for example, extraction of a recombinant protein, simplification of purification, or addition of biological functions. As described in US 2019-119662, an enzyme for use in the process of the present invention is advantageously produced by a transformant into which the recombinant DNA encoding the beta-galactosidase (EC 3.2.1.23) derived from *P. terrestris* is introduced, such that the gene exists as an exogenous molecule. Preferably, the transformant is prepared by transfection or transformation using the vector mentioned above. The host cell is not particularly limited as long as the present enzyme can be expressed, and it can be selected from, for example, *Bacillus* genus bacteria (e.g. *Bacillus subtilis, Bacillus licheniformis, Bacillus circulans*, etc.), lactic acid bacteria (e.g. *Lactococcus, Lactobacillus, Streptococcus, Leuconostoc, Bifidobacterium*, etc.), other bacteria (e.g. *Escherichia, Streptomyces*, etc.), yeast (e.g. *Saccharomyces, Kluyveromyces, Candida, Torula, Torulopsis, Pichia, Schizosaccharomyces*, etc.), and filamentous fungi (Eumycetes) (e.g. *Aspergillus* genus fungi such as *Aspergillus oryzae* and *Aspergillus niger*, *Penicillium* genus fungi, *Trichoderma* genus fungi, *Fusarium* genus fungi, etc.).

The process according to the present invention involves contacting a lactulose-containing feed with the beta-galactosidase at a preferred temperature of about 50-75° C., more preferably about 63-73° C., more preferably about 65-70° C.

The lactulose-containing feed preferably is an aqueous lactulose syrup comprising 40-58 wt. % lactulose, more preferably 45-55 wt. % lactulose, most preferably 50-55 wt % lactulose.

The pH of the lactulose-containing feed is preferably in the range 3.5-6.5, more preferably 4.5-6.0, and most preferably 5-5.5. The pH can be regulated by a food grade buffer, such as a citrate buffer, preferably in a concentration of 0.5 mM-10 mM.

The enzyme is used in a preferred concentration of at 1-20 LU/gram lactulose, more preferably 1-10 LU/gram lactulose, even more preferably of 2-8 LU/gram lactulose, and most preferably 3-6 LU/gram lactulose. Lower or higher concentrations can also be used, depending on the reaction temperature and reaction time: higher reaction temperature and/or longer reaction time allow lower enzyme concentrations.

The enzyme can be used in powder form (e.g. freeze dried, vacuum dried, or spray dried) or liquid form (e.g. dissolved in a phosphoric acid buffer solution, a triethanol amine buffer solution, a tris-hydrochloric acid buffer solution, or a GOOD buffer solution).

In a specific embodiment, the enzyme is used in immobilized form. Various ways of enzyme immobilization are known in the art. They typically comprise a porous carrier onto which the beta-galactosidase is immobilized via covalent binding, via physical absorption (charge-charge or *van der Waals* interaction), via gel encapsulation, or a combination thereof. Besides, carrier-free immobilized enzymes such as CLEC (cross-linked enzyme crystals) or CLEA (crosslinked enzyme aggregates) might be also applied.

Carriers that can promote direct covalent binding of the enzyme are preferred, in view of their ease of operation and absence of leakage into the reaction mixture. An example of a solid carrier is an activated acrylic polymer, preferably a functionalized polymethacrylate matrix. For example, a hexamethylenamino-functionalized polymethacrylate matrix (Sepabeads) or a microporous acrylic epoxy-activated resin, like Eupergit C 250 L, can be used.

The use of immobilized enzyme allows a repeated batch operating system involving several consecutive batches ('cycles') of GOS synthesis. It also allows for recycling of enzyme, which enables semi-continuous operation and multiple reuse of the enzyme.

The fGOS that is obtained from the process of the present invention can be isolated and purified using conventional methods, using, e.g., nanofiltration or sequential simulated moving bed (SSMB).

EXAMPLES

Beta-galactosidases of the following sources were used in the experiments:
*Aspergillus Oryzae* (Lactase 14 DS, ex-Amano Enzyme),
*Aspergillus Oryzae* (Tolerase 100, ex-DSM)
*Aspergillus Oryzae* (Biolactase F, ex-Kerry Bioscience)
*Papiliotrema terrestris* (β-galactosidase PT, ex-Amano Enzyme)

The general reaction conditions were as follows: 35 gram lactulose was added to 35 gram 0.01 M sodium citrate buffer, pH 6.5. Subsequently, enzyme was dissolved in 10 ml water and added to initialize the reaction. Of most enzymes, 20 lactose units (LU)/gram lactulose were used. However, Lactase 14 DS and Tolerase 100 were used in a concentration of 200 lactose units (LU)/gram lactulose, due to their low activity at the general reaction conditions used. The reaction mixtures were placed in a water bath with an orbital shaker, thermostated at 50° C. After 48 hours reaction, the reaction was quenched by adding 1.5% 1M HCl and subsequently heated at 95° C. for 30 minutes.

The fGOS content of the reaction mixtures was analyzed by HPLC (ThermoFisher Scientific Dionex type ICS 3000), based on the peak area percentage of individual sugars. The fGOS content was calculated by the following formula:

$$\text{fGOS content } (\%, ds) = 100\% - \text{galactose } \% - \text{glucose } \% - \text{lactose } \% - \text{lactulose } \% - \text{fructose } \%.$$

The fGOS content obtained with the different enzymes is summarized in Table 1. Table 1 shows that the enzyme obtained from *Papiliotrema terrestris* gave a far higher yield than the beta-galactosidase from *Aspergillus oryzae*; the best enzyme according to C. Guerrero et al.

The ratio between the two building blocks of lactulose, namely fructose and galactose, is used as an indicator of the enzyme performance. When the ratio is <1, it indicates that the fGOS content achieved cannot be increased anymore by prolonging the reaction time, because it can only hydrolyze the substrate or fGOS formed, as is the case with *Aspergillus oryzae*-derived beta-galactosidase. For the *P. terrestris*-derived beta-galactosidase, the ratio of fructose/galactose is above 2, suggesting that the fGOS yield can be further optimized with prolonged reaction time.

TABLE 1 fGOS composition formed by different beta-galactosidases

| Enzyme | Enzyme origin | Gal | Glu | Fruc | lactulose | fGOS* | Fruc/Gal |
|---|---|---|---|---|---|---|---|
| Lactase 14-DS | *Aspergillus Oryzae* | 23.68 | 2.51 | 24.54 | 11.86 | 37.41 | 1.04 |
| Tolerase 100 | *Aspergillus Oryzae* | 28.61 | 2.85 | 26.74 | 7.55 | 34.25 | 0.93 |
| Biolactase F | *Aspergillus Oryzae* | 26.34 | 2.78 | 25.88 | 9.2 | 35.8 | 0.98 |
| Amano PT | *Papiliotrema terrestris* | 5.22 | 1.99 | 11.63 | 27.59 | 53.57 | 2.23 |

*Estimated by the peak percentage of the mono sugars and the substrate left.

The HPLC chromatogram showed much more peaks for the fGOS produced by the *Papiliotrema terrestris*-derived enzyme compared to the fGOS produced with the *Aspergillus oryzae*-derived enzymes. Structure diversity of oligosaccharides is very important to serve the nutritional needs of the different bifidobacteria in the gut and the decoy function for binding pathogens. Therefore, the fGOS derived from the process of the present invention seems of higher nutritional value.

The degree of polymerization (DP) of the fGOS formed by the different enzymes is summarized in Table 2. Since it is not possible to distinguish lactulose from other DP2 fGOS components formed by lactulose, the total fGOS+lactulose content for each enzyme is given. Since lactulose itself is non-digestible (prebiotic) sugar, there is no need to separate it from fGOS. In the experiment with the *P. terrestris* enzyme, the fGOS+lactulose content is around 85%. In contrast, the fGOS+lactulose obtained from the *Aspergillus oryzae* enzymes is below 35%, which is probably due to the their intrinsic high hydrolytic activity as shown by their high mono sugar contents.

TABLE 2

DP composition of fGOS formed by different beta-galactosidases

| | Gal + Fru | Glc | DP2 | DP3 | DP4 | DP5 | DP6 | Mono sugars Gal + Glu + Fru | fGOS + lactulose |
|---|---|---|---|---|---|---|---|---|---|
| Lactase 14-DS | 68.1 | 0.12 | 20.72 | 6.1 | 1.68 | 0.54 | 0.19 | 68.22 | 31.78 |
| Biolactase F | 75.38 | 0 | 18.73 | 3.68 | 0.71 | 0.14 | 0.03 | 75.38 | 24.62 |
| Tolerase too | 81.59 | 0.2 | 13.64 | 1.99 | 0.25 | 0 | 0 | 81.79 | 18.21 |
| Amano PT | 13.77 | 0.89 | 59.54 | 19.74 | 2.76 | 0.59 | 0 | 14.66 | 85.34 |

The experiment with *P. terrestris* was repeated with lactose as the substrate. The results are displayed in Table 3. It shows that the DP2-content of the fGOS (obtained from lactulose) is significantly higher than that of GOS obtained from lactose.

This high DP2 fGOS component may constitute an advantage for the infant gut microbiota, because the growth of infant type of bifidobacteria such as B. *Breve* in the infant colon may be selectively promoted.

TABLE 3

Comparison of Lactose-GOS and Lactulose GOS formed by *P. Terrestris* beta-galactosidase

| Substrate | Glc | DP2 | DP3 | DP4 | DP5 | DP6 | Mono sugars Gal + Glu + Fru | GOS + lactulose |
|---|---|---|---|---|---|---|---|---|
| Lactulose | 0.89 | 59.54 | 19.74 | 2.76 | 0.59 | 0 | 14.66 | 85.34 |
| Lactose | 20.04 | 39.3 | 24.45 | 11.35 | 2.26 | 0.23 | 22.23 | 60 |

The invention claimed is:

1. A process for the preparation of a galacto-oligosaccharide preparation, which process comprises the step of contacting a lactulose-containing feed with a beta-galactosidase (EC 3.2.1.23) derived from *Papiliotrema terrestris*.

2. The process Process-according to claim 1 wherein the beta-galactosidase is derived from *Papiliotrema terrestris* strain MM13-F2171 (Accession Number: NITE BP-02177) or APC-6431 (Accession Number: NITE BP-02178).

3. The process according to claim 1 wherein the beta-galactosidase comprises an amino acid sequence according to any of SEQ ID NO: 1, 2, 3 or 4, or an amino acid sequence that is at least 80% identical to any of SEQ ID NO: 1, 2, 3 or 4.

4. The process according to claim 1 wherein the lactulose-containing feed comprises 40-58 wt. % lactulose.

5. The process according to claim 1 wherein the pH of the lactulose-containing feed is in the range 3.5-6.5.

6. The process according to claim 1 wherein the beta-galactosidase is used in a concentration of 1-20 LU/gram lactulose.

7. The process according to claim 1 wherein the lactulose is reacted with the beta-galactosidase at a temperature in the range 50-75° C.

8. A galacto-oligosaccharide preparation obtained by the process of claim 1.

9. A galacto-oligosaccharide preparation that is clinically free from lactose and which comprises, based on dry matter, 30-60 wt % of galacto-oligosaccharides other than lactulose.

10. The galacto-oligosaccharide preparation according to claim 9 comprising, based on dry matter, 40-70 wt % of a mixture of lactulose and monosugars.

11. A nutritional composition comprising the preparation according to claim 8, for administration to a subject known to suffer or having an increase chance to suffer from hypersensitivity to a GOS preparation obtained by transgalactosylation of lactose using a beta-galactosidase derived from *Bacillus circulans* or from *Aspergillus oryzae*.

12. A nutritional composition comprising the preparation according to claim 8, for administration to a subject known to suffer or having an increase chance to suffer from lactose intolerance.

13. A nutritional composition comprising the galacto-oligosaccharide preparation according to claim 8 and at least one further ingredient selected from the group consisting of a protein source, probiotics, LC-PUFA's and carbohydrates.

14. The nutritional composition according to claim 13 wherein said composition is suitable for consumption by adults and children aged at least 18 months.

* * * * *